United States Patent [19]
Gadbut

[11] Patent Number: 5,945,297
[45] Date of Patent: Aug. 31, 1999

[54] PROCESS FOR SCREENING CANDIDATE AGENTS THAT MODULATE THE HEMOSTATIC SYSTEM

[75] Inventor: Albert P. Gadbut, San Mateo, Calif.

[73] Assignee: MetaXen LLC, Hayward, Calif.

[21] Appl. No.: 09/069,888

[22] Filed: Apr. 29, 1998

[51] Int. Cl.$^6$ .............................. C12Q 1/56; G01N 33/86; G01N 33/48; G01N 21/76
[52] U.S. Cl. .............................. 435/13; 436/69; 436/172; 424/529; 424/531; 424/532; 530/381; 530/382
[58] Field of Search .................................. 435/13; 436/69, 436/172; 424/529, 531, 532; 530/381, 382

[56] References Cited

U.S. PATENT DOCUMENTS

| | | | |
|---|---|---|---|
| 3,772,504 | 11/1973 | Sawyer | 364/477.03 |
| 5,125,069 | 6/1992 | O'Boyle | 392/465 |
| 5,314,826 | 5/1994 | Baugh | 436/69 |
| 5,567,596 | 10/1996 | Diamond et al. | 435/13 |
| 5,599,663 | 2/1997 | Vaughn | 435/6 |
| 5,736,313 | 4/1998 | Spargo et al. | 435/2 |

OTHER PUBLICATIONS

Kelton, et al. J. Lab. Clin. Med. (Apr. 1984); 103(4), pp. 606–612.

Michelson, A.E. Blood Coag. Fibrinol. (1994); 5, pp. 121–131. No month found.

Charlton et al. (1996), "Evaluation of a Low Molecular Weight Modulator of Human Plasminogen Activator Inhibitor–1 Activity," *Thrombosis and Haemostasis* 75(5):808–815.

Charlton et al. (1997), "XR5118, A Novel Modulator of Plasminogen Activator Inhibitor–1 (PAI–1), Increases Endogenous tPA Activity in the Rat," *Fibrinolysis & Proteolysis* 11(1):51–56.

Krishnamurti et al. (1994), "Inhibitory Effects of Lysine Analogues on t–PA Induced Whole Blood Clot Lysis," *Thrombosis Res.* 73(6):419–430.

Lozano et al. (Apr. 1997) "Loss of High-affinity Thrombin Receptors During Platelet Concentrate Storage Impairs the Reactivity of Platelets to Thrombin," *Transfusion* 37:368–375.

Taylor et al. (1973), "Coagulolysis: Mechanism of Formation and Lysis of Dilute Whole Blood Clots and Application of this Assay into Study of Certain Hypercoagulable States," *Ser. Haemat* VI:528–548.

*Primary Examiner*—Kathleen K. Fonda
*Assistant Examiner*—Marjorie Moran
*Attorney, Agent, or Firm*—Carol L. Francis; Bozicevic, Field & Francis

[57] ABSTRACT

The present invention provides a method for screening candidate agents to identify compounds that modulate the hemostatic system. The method of the invention involves a screening medium comprised of stored whole blood, preferably diluted with buffer, to which unrefrigerated platelets have been added. Candidate agents that may inhibit or activate clot formation or clot lysis are added to the screening medium and suitable compounds are identified. The assay provided is physiologically relevant, rapid, inexpensive and allows for large scale screening of candidate agents.

31 Claims, 6 Drawing Sheets

5,945,297

PROCESS FOR SCREENING CANDIDATE AGENTS THAT MODULATE THE HEMOSTATIC SYSTEM

TECHNICAL FIELD

The present invention relates generally to the screening of candidate agents that modulate the hemostatic system. More specifically, the invention pertains to an assay for screening candidate agents that inhibit or activate clot formation, or clot lysis in the hemostatic system. The method involves the use of stored whole blood to which fresh platelets have been added.

BACKGROUND

The normal hemostatic system limits bleeding and thrombosis by precisely regulated interactions between components of the blood vessel wall, circulating blood platelets and plasma proteins (see, e.g., Harrison's "Principles of Internal Medicine" (1997) $14_{th}$ Edition, Fauci et al. (eds.), Mc Graw Hill, New York). Disruption in either of the two processes of the hemostatic system—clot formation and clot lysis—can have severe medical repercussions. Hemorrhage, thrombosis and embolism are all common clinical manifestations of many diseases. Thus, the ability to efficiently screen a large number of candidate agents for their ability to modulate clot formation, or clot lysis (thrombolysis) would greatly increase the therapeutic repertory currently available to treat such conditions.

The clotting cascade of the hemostatic process is initiated when trauma, surgery or disease disrupt the vascular endothelial lining and blood is exposed to subendothelial connective tissue. The injured vascular endothelial cell releases substances that initiate the clotting cascade, a process involving the activation of a series of compounds that ultimately results in the conversion of prothrombin to thrombin. Thrombin is a key enzyme in the coagulation event, catalyzing the activation of platelets and the cleavage of fibrinogen.

While formation of fibrin monomers provides the structural matrix of a clot, aggregation of platelets is critical for the clot's integrity. Upon activation by thrombin, the platelet expresses on its surface the IIb/IIIa receptor, which allows for the binding of von Willebrand Factor. The binding of von Willebrand Factor to the IIb/IIIa receptor of adjacent platelets results in the platelet aggregation reaction.

Platelets are small disc-shaped cell fragments formed by the breakdown of megakaryocytes, and are very susceptible to changes in their environment such as pH and temperature. In normal blood banking procedures, donated whole blood is stored at a temperature of approximately 4° C. Upon refrigeration, the platelet irreversibly changes its structural conformation from a disc shape to a sphere. When the platelet is not in the normal disc shape, it is incapable of aggregation and thus not physiologically relevant. In addition to the activation of platelets, thrombin also acts on fibrinogen, the key structural protein in blood clot formation and the substrate for thrombin proteolytic activity. Thrombin catalyzes the release of small peptides, fibrinopeptides A and B, from the chains of fibrinogen. The removal of the fibrinopeptides from the fibrinogen substrate results in the formation of fibrin monomers which polymerize into fibers and provide the structural matrix of the clot. The clot formed by fibrin is removed or degraded by the process of fibrinolysis. Fibrinolysis is initiated by the release of either tissue plasminogen activator or prourokinase from endothelial cells. These agents convert plasminogen into the active proteolytic enzyme, plasmin which catalyzes the fibrin substrate into soluble degradation products. In addition, plasmin is enzymatically active against fibrinogen, and degrades fibrinogen into soluble products.

Various methods for assaying candidate agents that modulate the formation, inhibition, or degradation of clots have been described previously (Taylor et al. (1973) Ser. Haemat. VI:528; Krishnamurti et al. (1994) Thrombosis Research 73:419; Charlton et al. (1996) Thrombosis and Haemostiasis 75:808). However, previously known assays only utilized blood isolated from on-site donors, either human or animal. Consequently, the scale and frequency of candidate agents to be screened were limited by the availability of on-site donors. Thus, there is a significant need for a physiologically relevant, rapid, and inexpensive assay to determine the potential of candidate drugs to modulate clot formation or clot lysis. The subject application provides such a method.

SUMMARY OF THE INVENTION

The present invention is directed to an assay for the screening of candidate agents that modulate the hemostatic system. In particular, a dilute blood assay is provided that may be used to screen for the potential of candidate agents to modulate the hemostatic system, i.e., that either activate or inhibit components of the hemostatic system, such as components involved in clot formation or clot lysis.

Accordingly, it is a general object of this invention to provide an assay for the screening of candidate agents that modulate a component of the hemostatic system.

It is another object of this invention to provide an assay for the screening of candidate agents that either inhibit or promote clot lysis.

It is still another object of this invention to provide an assay for the screening of candidate proteases that either inhibit or promote clot lysis.

It is yet another object of this invention to provide an assay for the screening of candidate drugs that either inactivate or stimulate tissue plasminogen activator (tPA).

It is yet another object of this invention to provide an assay for the screening of candidate agents that inhibit or activate clot formation.

It is a further object of this invention to provide an assay for the screening of candidate proteases that inhibit or activate clot formation.

Additional objects, advantages and novel features of the invention will be set forth in part in the description which follows, and in part will become apparent to those skilled in the art upon examination of the following, or may be learned by practice of the invention.

A feature of this invention is that the assay may be performed without the use of fresh blood thereby obviating the need for on site donors. Additional features are the rapidity, accuracy, large-scale screening capability and cost effectiveness of the instantly disclosed assay.

DETAILED DESCRIPTION OF THE INVENTION

Figure 1:
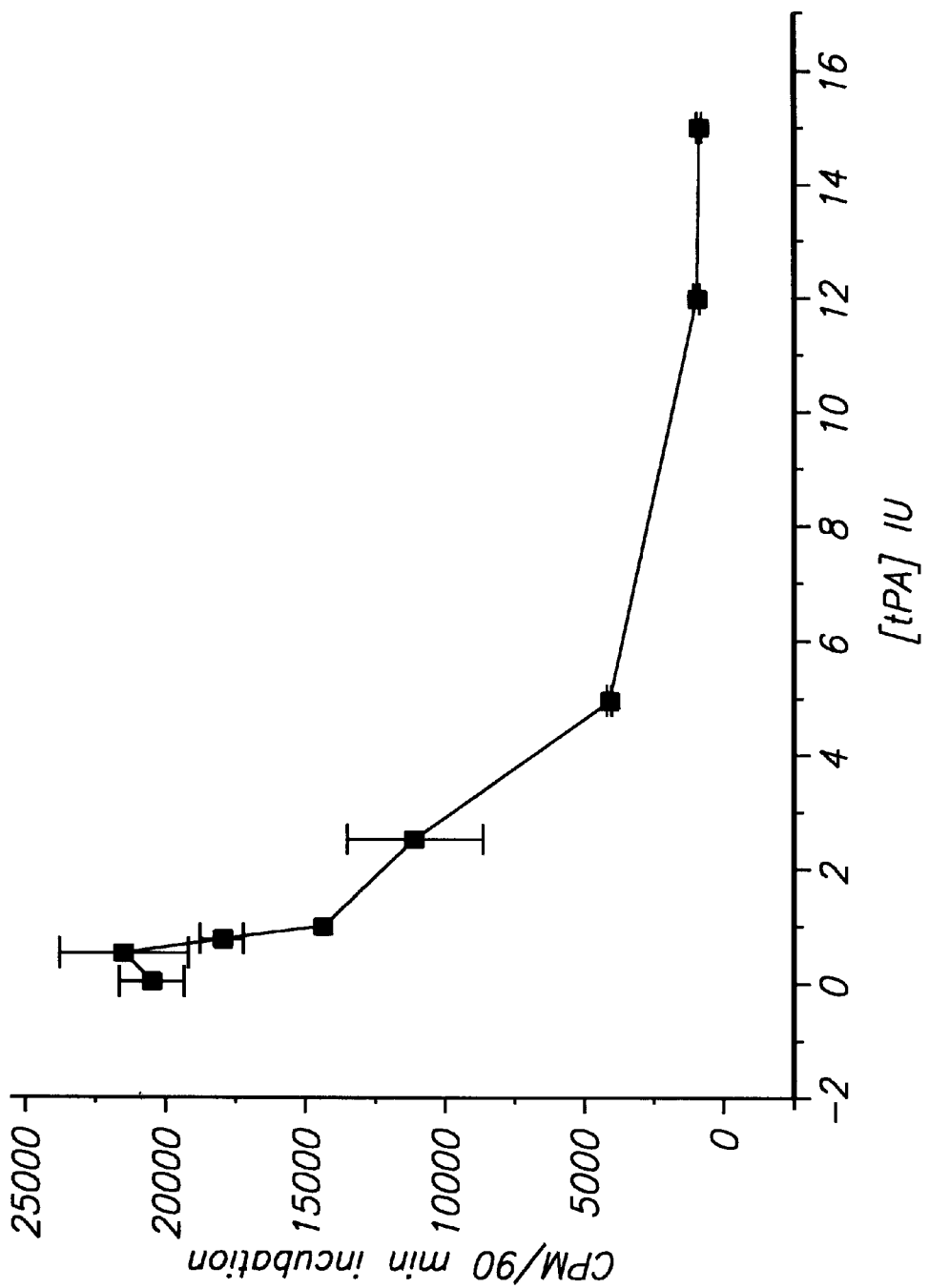
FIG. 1 is a graph showing the concentration-dependent activity of tPA on clot lysis following a 90 minute incubation. As the clot is lysed, less [$^{125}$I]-labeled fibrin is detected in the clot. The Y axis represents the total [$^{125}$I]-labeled fibrin remaining in the clot after 90 min. The X axis represents the concentration of tPA. As the concentration of tPA increases, total clot lysis is increased as well.

Before the present invention is described in detail, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and" and "the" include plural referents unless the context clearly dictates otherwise. Thus, for example, reference to "a candidate agent" includes a plurality of such agents and reference to "a protease inactivator" includes two or more protease inactivators and equivalents thereof known to those skilled in the art, and so forth.

Unless defined otherwise, all technical and scientific terms used herein have the same meaning as commonly understood to one of ordinary skill in the art to which the invention pertains. Although any methods, devices and materials similar or equivalent to those described herein can be used in the practice or testing of the invention, the preferred methods, devices and materials are now described. All publications mentioned herein are incorporated herein by reference to disclose and describe the methods and/or materials in connection with which the publications are cited.

Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

In this specification and in the claims which follow, reference will be made to a number of terms which shall be defined to have the following meanings:

By "a component of the hemostatic system" is meant any molecule or functional equivalent thereof that either directly or indirectly has a role in the hemostatic system, such as nucleosides, lipids, peptides or proteins. Examples include, but are not limited to, serine proteases like tissue-type plasminogen activator (tPA), urokinase or urinary-type plasminogen activator (uPA), plasmin, kallikrein, thrombin, Factors VIIa, IXa, Xa, XIa and XIIa, serine protease inhibitors, such as plasminogen activator inhibitor-1 (PAI-1), PAI-2 and PAI-3, α-2-antiplasmin, antithrombin III, and heparin cofactor I.

By "modulating" the hemostatic system is meant having an effect on one or more of the precisely regulated interactions between components of the blood vessel wall, circulating blood platelets and plasma proteins. Generally, a compound which "modulates" the hemostatic system, as used herein, is meant a compound which has the ultimate effect of either inhibiting or promoting clot lysis, or a compound which has the ultimate effect of either inhibiting or promoting clot formation.

By "clot formation" is meant formation of either (a) a fibrin clot, or (b) a "complete" clot in which a fibrin clot is formed and platelet aggregation is observed as well.

By an "inactivator" of a protein is meant an agent which inactivates a protein of the hemostatic system by blocking, impeding, disrupting, inhibiting, competing with, interfering with or otherwise preventing completely or in part the action of that protein.

By an "activator" of a protein is meant an agent which activates a protein of the hemostatic system by enhancing, restoring or otherwise replacing the action of that protein.

By "stored whole blood" is meant whole blood stored by conventional blood banking techniques. Generally, although not necessarily, such blood is stored at a temperature in the range of approximately 4° C. to about 6° C. Also intended to be included are fractions of whole blood that have been generated from isolated and stored blood components, such as concentrates or platelet phoresis units.

By "unrefrigerated" as used to refer to the platelets that are added to the stored whole blood in the method of the invention is meant platelets that have been stored and a temperature not lower than approximately 20° C.

The present invention relates to a method for screening candidate agents that modulate one or more components of the hemostatic system, in particular components involved in clot formation or clot lysis. According to the present invention, a dilution of stored whole blood to which fresh, unrefrigerated platelets have been added is the medium used to screen a candidate agent. The use of stored whole blood obviates the need for obtaining fresh blood from on-site donors, thus allowing for large-scale screening of candidate agents that modulate a component of the hemostatic system. The assay can be used to screen any number of candidate agents for their ability to modulate hemostatic proteins. Specific, non-limiting examples illustrating various ways in which the present invention may be used, and various candidate agents that may be screened therewith, are set forth following this section.

Stored whole blood may be obtained, for example, from any blood bank. Stored whole blood processed by conventional blood banking techniques has a shelf life of about 45 days. Preferably, the whole blood used in the present method has been stored for between approximately 3 and 21 days, more preferably between approximately 3 and 10 days.

Standard techniques used in blood banking or storage generally involve storing whole blood at a temperature in the range of approximately 4° C. and 6° C., preferably closer to 4° C., and storing platelets at a temperature in the range of approximately 20° C. to 30° C., preferably at about 25° C. Such storage may alter the activity of components present in whole blood; for example, platelets are inactivated by refrigeration. As platelets are integral to the normal functioning of the hemostatic system, fresh, unrefrigerated platelets must be added to the stored whole blood for use in the subject assay. Without adding unrefrigerated platelets to stored whole blood, complete clots—involving formation of a fibrin clot as well platelet aggregation—will not form regardless of the concentration of exogenously added thrombin. In the presence of thrombin, refrigerated whole blood will form a fibrin clot; there will, however, be no platelet aggregation without addition of unrefrigerated platelets as provided herein. The method of the invention is premised, in part, on the recognition that platelet aggregation is as important as the fibrin clot in normal clot formation.

Platelets may be obtained from, for example, any blood bank. Preferably, platelets that have been stored for about 3 days to 10 days, more preferably from about 3 days to 8 days, are added to the whole blood. The ratio of stored whole blood to platelets may vary. Generally, although not necessarily, on the order of $10^6$ to $10^8$ platelets may be added to 1 mL of whole blood; this typically represents an approximately 1:1 ratio by volume.

For optimization of the assay, it is preferred that the whole blood be diluted prior to use in the screening assay. The blood may be diluted with any buffer at physiological pH. Examples of suitable buffers include, but are not limited to, phosphate buffers. The blood may be diluted with the buffer at a ratio of blood to buffer in the range of about 1:5 (vol/vol) to about 1:20 (vol/vol) prior to the addition of the platelets.

The combination of stored whole blood to which unrefrigerated platelets have been added provides the basic medium in which the candidate agents are to be screened. One skilled in the art will appreciate that stored whole blood or platelets may be used outside the suggested ranges, but the assay may not function as effectively.

The whole blood, preferably diluted whole blood, to which platelets have been added, can be used to screen candidate agents by otherwise conventional methodology (Taylor et al. (1973) *Ser. Haemat.* VI:528; Krishnamurti et al. (1994) *Thrombosis Research* 73:419; Charlton et al. (1996) *Thrombosis and Haemostasis* 75:808, herein incorporated by reference). One of skill in the art will appreciate that depending on the particular component of interest involved in the hemostatic system, additional materials may be incorporated into the screening medium. The concentration of each added material is determined in part but not exclusively by the characteristics of the given lot of blood products used as a screening media at the time.

Thus, for example, the screening of candidate agents that inhibit PAI-1 activity, may require the addition of thrombin, tPA and PAI-1. Alternatively, screening for candidates that promote clot formation may require the addition of tissue factor, Factor XIIa, XIa, IXa, VIII, Xa or thrombin. The effect of the candidate agent on the component of interest in the hemostatic system may be evaluated, as noted above, by conventional methodology. For example, the ability of a candidate agent to inhibit PAI-1 activity may be assessed directly by monitoring the activity of PAI-1 enzyme itself using a calorimetric assay such as the S-2288 assay sold by Chromogenix, Moindal, Sweden. Alternatively, the ability of a candidate agent to inhibit PAI-1 may be assessed indirectly by examining clot lysis. For example, a trace amount of labeled fibrinogen may be added to the assay prior to addition of the candidate agent. The labeled fibrinogen will be incorporated into the clot during clot formation. If the candidate agent inhibits PAI-1 activity, there should be a decrease in label incorporated into the clot during clot lysis and an increase in label in the buffer solution. The fibrinogen may be labeled by any conventional methodology. Examples of suitable labels include radioactive labels such as $^{125}I$, $^{35}S$, $^{14}C$, $^{32}P$, $^{33}P$, $^{3}H$, and the like. Fluorescent labels may be used as well. As will be appreciated by those skilled in the art, suitable fluorescent labels include, but are not limited to, fluorescein and fluorescein derivatives such as carboxyfluorescein, fluorescein acrylamide, fluorescein isothiocyanate, coumarin, seminaphthorhodafluorescein, seminaphthofluorescein, naphthofluorescein, hydroxypyrene trisulfonic acid and dichlorofluorescein.

The assay of the subject invention may be used in functional studies, to determine the effect of any candidate agent on the blood clotting cascade or clot lysis. The term "candidate agent" as used herein describes any molecule or group of molecules, e.g., peptides, proteins, small molecules, or the like, suspected of having the capability of modulating the blood clotting cascade. Generally, each candidate agent is screened at several different concentrations, typically run in parallel, in order to obtain differential responses at each concentration. Normally, one of the concentrations serves as a positive or negative control.

Suitable candidate agents encompass compounds of numerous and varied chemical classes, although typically they are organic molecules, preferably small organic compounds having a molecular weight of more than about 50 and less than about 2,500 Daltons. Candidate agents contain functional groups necessary for interaction with one or more components involved in the hemostatic system, e.g., proteins, nucleic acids and the like. Candidate agents are also found among biomolecules including, but not limited to, peptides, saccharides, fatty acids, steroids, purines and pyrimidines, and derivatives, structural analogs or combinations thereof. Candidate agents are obtained from a wide variety of sources including libraries of synthetic or natural compounds. Alternatively, libraries of natural compounds in the form of bacterial, fungal, plant and animal extracts are commercially available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

By way of example, particularly useful candidate agents to identify are those capable of modulating serine protease activity. For example, the chymotrypsin superfamily of serine proteases includes several proteases involved in regulating the hemostatic system, e.g., tissue-type plasminogen activator (tPA), urokinase or urinary-type plasminogen activator (uPA), plasmin, and clot cascade proteases including kallikrein, thrombin, and Factors VIIa, IXa, Xa, XIa and XIIa. The specificity of the bonds cleaved by these proteases ranges from the very broad, as in plasmin, to the extremely specific, as, for example, in the case of the clotting cascade enzymes. The activity of these proteases is regulated at several levels. Many of these proteases are produced in inactive, or zymogen, forms. The zymogen forms can be activated, for example, by cleavage of inhibitory domains within the molecules, thereby permitting the proteolytic activity of the enzyme to be revealed (for example, the cleavage of plasminogen to plasmin can be catalyzed by either uPA or tPA). Another means by which the activity of serine proteases is regulated involves polypeptides that directly inhibit proteolytic activity. Inhibition is accomplished by employing a protein structure which fits within the active site of a particular serine protease. Therefore, examples of serine protease inhibitors that can be screened by the instant method include, but are not limited to, the bovine pancreatic trypsin inhibitor ("BPTI") family (e.g., snake venom inhibitor, inter-alpha inhibitor, and the A4 amyloid precursor "A4695"), the Kazal family (e.g., pancreatic secretory inhibitor, ovomucoid, and seminal plasma acrosin inhibitor), the Streptomyces subtilisin family (e.g., from *S. albogriseolus*, and plasminostreptin), the serpin family (e.g., plasminogen activator inhibitor-1 (PAI-1), PAI-2, PAI-3, C1 esterase inhibitor, α-2-antiplasmin, contrapsin, α-1-antitrypsin, antithrombin III, protease nexin I, α-1-antichymotrypsin, protein C inhibitor, heparin cofactor II and growth hormone regulated protein), the soybean trypsin inhibitor family (e.g., soybean trypsin inhibitor), the potato inhibitor family (e.g., potato inhibitor, barley chymotrypsin inhibitor, and leech inhibitor eglin), and the Bowman-Birk inhibitor family (e.g., Lima bean inhibitor IV, garden bean inhibitor, and adzuki bean inhibitor II).

Alternatively, because thrombolytic agents are increasingly used in the prevention and/or dissolution of formed thrombi such as in acute myocardial infarction or stroke, it would be useful to identify candidate agents that inhibit the ability of PAI-1 to inactivate tPA- and uPA-catalyzed conversion of plasminogen to plasmin. Potential candidate agents to be screened may be selected from diketopiperazine compounds or derivatives or analogs thereof (see, e.g., International Patent Publ. Nos. WO 95/21832, WO 95/32190, WO 95/21829 and UK Patent GB 2 284 420 B, Bryans et al. (1996) *J Antibiotics* 49:1014, Charlton et al. (1996) *Thrombosis and Haemostasis* 75:808, Charlton (1997) *Exp. Opin. Invest. Drugs* 6:539, Charlton (1997) *Drugs of the Future* 29:45, and Charlton et al.(1997) *Fibrinolysis & Proteolysis* 11:51).

Candidate agents identified as suitable drugs using the screening process of the invention may be used to treat any medical conditions whose treatment would be benefitted by modulation of blood clot lysis. These conditions include, but are not limited to, thromboembolic disorders, prophylaxis of undesired clotting as a result of surgery, post-surgical maintenance of grafts or prostheses, congestive heart failure, cardiomyopathy, myocardial infarction, cerebrovascular disease, acute venous thrombosis, pulmonary embolism, atherosclerosis, ventricular or atrial thrombi, peripheral or mesenteric arterial thrombosis, acute coronary infarction or occlusion, and acute peripheral artery occlusion. The candidate agents identified as suitable drugs may also be administered against thromboemboli associated with major surgery, congestive heart failure, cardiomyopathy, myocardial infarction, pregnancy, or disseminated intra vascular coagulation.

Some patients who have very limited ability to form clots could also benefit from a candidate agent that has been screened using the process of the invention as a suitable drug for promoting the clotting cascade. Examples of diseases or disorders where such drugs would have therapeutic potential, include, but are not limited to afibrinogenemia, dysfibrinogenemia, hypoprothrombinemia, parahemophelia, hypoconvertinemia, hemophilia A, hemophilia B, Stuart-Prower factor deficiency, plasma thromboplastin antecedent deficiency, Hageman trait, thrombocytopenia, disorders of platelet function, von Willebrand's disease, hepatic dysfunction, circulating anticoagulants, inherited defects in natural coagulation inhibitors (such as antithrombin, protein C, or protein S), dysplasminogenemia, defective release or diminished venous content of plasminogen activator, excessive release of PAI, heparin cofactor II deficiency, homocystinuria, chronic congestive heart failure, metastatic tumor or malignancy, extensive trauma or major surgery, myeloproliferative disorders, or treatment with oral contraceptives or L-asparaginase.

Thus, the candidate agents determined by the method of the invention to effectively modulate clot formation or clot lysis may be administered therapeutically to a subject. Once identified, the candidate agent will generally be incorporated into a pharmaceutical preparation suitable for a particular mode of administration, e.g., a sterile injectable aqueous or oleaginous suspension, an oral formulation that may be a liquid, tablet, capsule, or the like, a preparation suitable for topical or transdermal application, a rectal suppository, or the like. Such formulations may be prepared by conventional methodology known to those skilled in the art.

The aforementioned compositions may contain more than one active agent, i.e., an additional active agent may be included along with the selected candidate agent identified using the process of the invention. These may be known clotting or thrombolytic agents or other types of therapeutic compounds.

The regimen for administration of the selected candidate agent determined to modulate hemostasis will necessarily be dependent upon the needs of the individual subject being treated, the type of treatment, and the judgment of the attending practitioner. Generally, the dosage regimen will follow that used in conjunction with the administration of known agents useful for disorders or diseases involving the clotting cascade.

The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired effect is to be achieved), orally, or by any other desirable means. The candidate agent can be administered singly or in combination with one or more other candidate agents and/or other therapeutic agents as noted above, particularly when administration of a combination of agents may result in a synergistic effect. The effect of agent administration upon a subject can be monitored by conventional methodology.

It is to be understood that while the invention has been described in conjunction with the preferred specific embodiments thereof, the description above and the experimental section which follows are intended to illustrate and not limit the scope of the invention. Other aspects, advantages and modifications within the scope of the invention will be apparent to those skilled in the art to which the invention pertains.

EXPERIMENTAL

The following examples are put forth so as to provide those of ordinary skill in the art with a complete disclosure and description of how to use the screening process of the invention. Efforts have been made to ensure accuracy with respect to numbers (e.g., amounts, temperature, etc.) but some errors and deviations should be accounted for. All starting materials and reagents are commercially available.
Materials:

Compatibility matched QNS (quantity non-sufficient) whole blood and outdated single platelet packs were purchased from Peninsula Blood Bank (Burlingame, Calif.). Two-chain tPA was purchased from Biopool (Umea, Sweden). Fibrinogen ($^{125}$I) 7.38 MBq/mg, 110 $\mu$Ci was purchased from Amersham (Arlington Heights, Ill.). Thrombin and low molecular weight heparin were purchased from Sigma (St. Louis, Mo.). Optiphase Supermix scintillation cocktail was purchased from Wallac (Turku, Finland). Anti-PAI-1 monoclonal Ab 3783 was from American Diagnostica, Inc. (Greenwich, Conn.). Anti-PAI-1 peptide was purchased from Peninsula Laboratories (Belmont, Calif.).

Titration of tPA for Complete Fibrinolysis:

Platelets (150 $\mu$l) were added to 1.2 ml hypotonic phosphate buffer, containing 53 mM $Na_2HPO_4$ and 12 mM $KH_2PO_4$. To this solution 150 $\mu$l whole blood (less than 23 days old), supplemented with ~120 nCi [$^{125}$I]-labeled fibrinogen, was added followed by the addition of tPA (0.5–15 IU). The reaction was gently mixed in a 17×100 mm polypropylene tube in the presence of 1.25 units thrombin. After 5 min. or upon clot formation the tubes were gently shaken to dislodge the clots from the side of the tubes to hasten retraction. After 90 min. the reaction was terminated by the addition of 10 ml phosphate buffer. The diluted reaction volume was immediately poured over a 25 mm Whatman GF/C filter. The filters were washed with an additional 5 ml phosphate buffer, and then dried at 55° C. for 30 min. and scintillation counted. Fibrinolysis was measured as the difference between total counts in the reaction and total counts remaining on the filters. The reactions were carried out a minimum of four times in duplicate. Results are illustrated in FIG. 1, a graph showing the concentration-dependent activity of tPA on fibrinolysis. The Y axis represents the total [$^{125}$I]-labeled fibrin remaining in the clot after 90 minutes, and the X axis represents the concentration of tPA. As the clot is lysed, less [$^{125}$I]-labeled fibrin is detected in the clot, and as the concentration of tPA increases, total clot lysis is increased as well.

Figure 2:
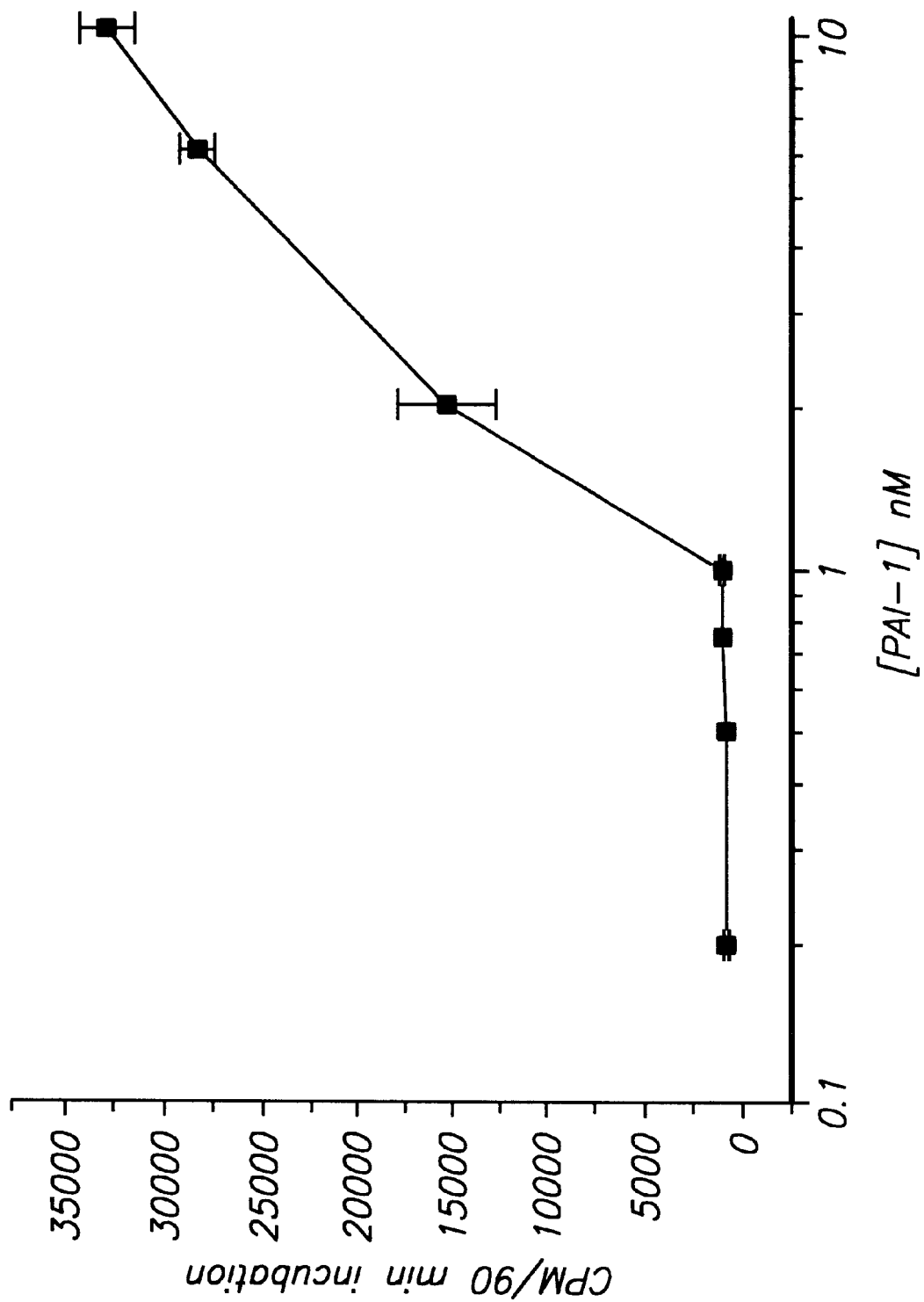
FIG. 2 is a graph showing the effect of PAI-1 (plasminogen activator inhibitor) concentration to inhibit a single concentration of tPA within 90 min. The Y axis represents the total [$^{125}$I]-labeled fibrin remaining within the clot. The X axis represents the concentration of PAI-1. As the concentration of PAI-1 increases, total clot lysis decreases.

Titration of PAI-1 to Inhibit a Single Concentration of tPA:

To determine the concentration of PAI-1 necessary to completely inhibit a single concentration of tPA capable of producing total clot lysis, a titration of PAI-1 was established. The reactions were set up in the same order as described above with the exception that each tube was given 12 IU tPA. Following the addition of tPA and prior to the addition of thrombin each tube was treated with a single concentration of PAI-1 in the range of 0.2 to 10.0 nM. After the addition of thrombin (1.25 units) the reaction tubes were treated as described above. Results are illustrated in FIG. 2, a graph showing the effect of PAI-1 concentration on inhibition of tPA. The Y axis represents the total [$^{125}$I]-labeled fibrin retained within the clot, and the X axis represents the concentration of PAI-1. As may be seen, as the concentration of PAI-1 increases, total clot lysis decreases.

Figure 5:
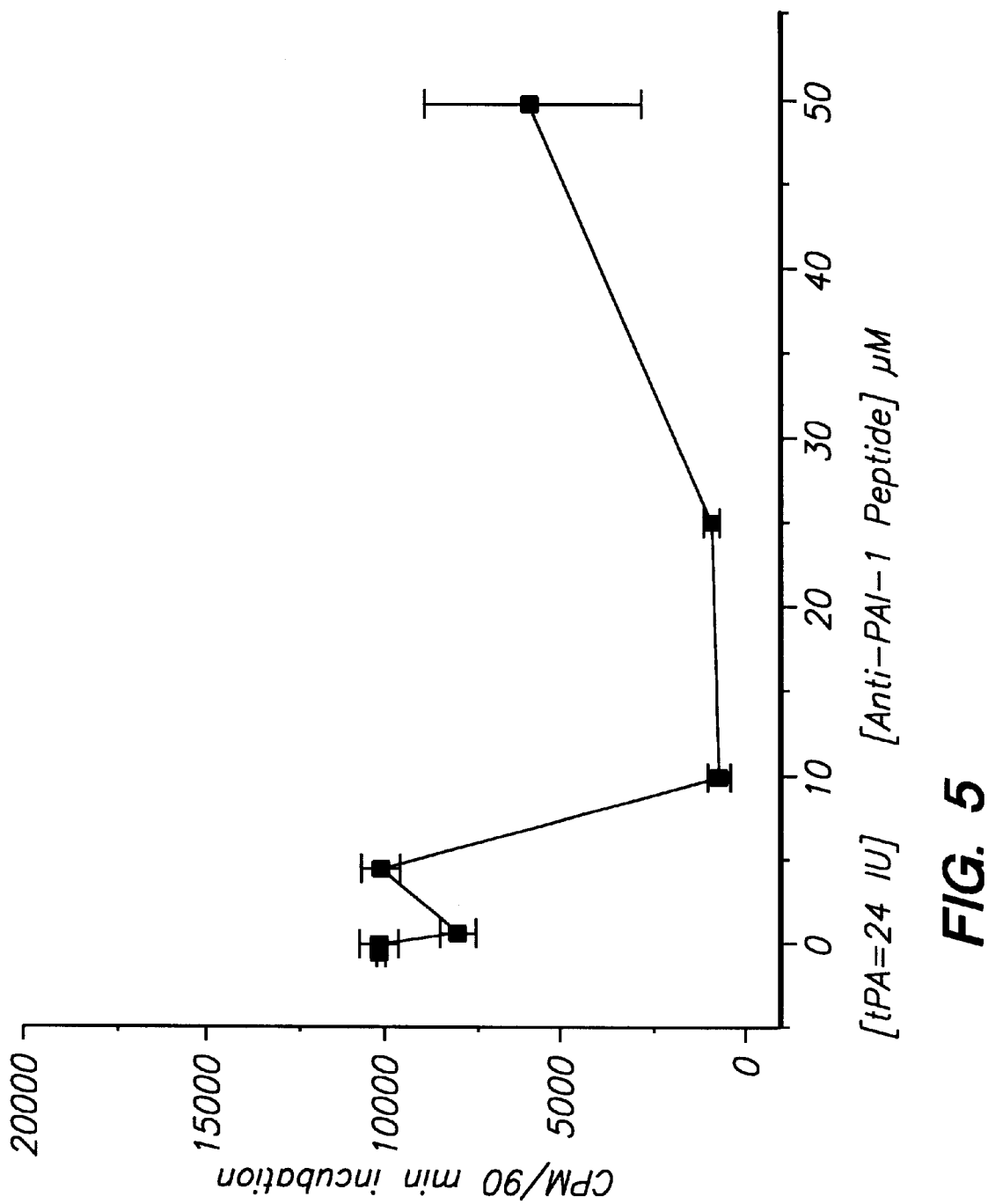
FIG. 5 is a graph showing inhibition of PAI-1 by an anti-PAI-1 peptide. The Y axis represents the total [$^{125}$I]-labeled fibrin remaining within the clot after 90 min. The X axis represents the effect of a single concentration of tPA and a single concentration of PAI-1 in the presence of increasing concentrations of anti-PAI-1 peptide.

Titration of Anti-PAI-1 Peptide to Inhibit PAI-1 Activity:

To demonstrate the use of the assay of the invention as a potential screen for inhibitors of thrombotic molecules such as PAI-1, the effect of a PAI-1 inhibitor, an anti-PAI-1 peptide, was evaluated for its capability to reduce PAI-1 inhibition of tPA. The anti-PAI-1 peptide is a fourteen amino acid peptide homologous to the α segment of the active loop of the PAI-1 molecule. This peptide is reported to inhibit the function of PAI-1 at 50 $\mu$M in a dilute blood clot lysis assay using classical methods (see Eitzman et al. (1995) *J. Clin. Invest.* 95:2416–2420). In this assay the addition of buffer, platelets and [$^{125}$I]-labeled fibrinogen supplemented whole blood was added as described above. In each reaction tube 24 IU tPA was added followed by 1.2 nM PAI-1 15 min. preincubation +/−anti-PAI-1 peptide (0.5–50 $\mu$M). Each reaction was gently mixed and 1.25 units thrombin was added. After 90 min. reaction time, samples were treated as described above. Results are illustrated in FIG. 5, a graph illustrating inhibition of PAI-1 by the anti-PAI-1 peptide. In the graph, the Y axis represents the total [$^{125}$I]-labeled fibrin retained within the clot after 90 min., and the X axis represents the effect of a single concentration of tPA and a single concentration of PAI-1 in the presence of increasing concentrations of the anti-PAI-1 peptide. At a concentration of 10 $\mu$M, complete inhibition of PAI-1 was observed.

Figure 3:
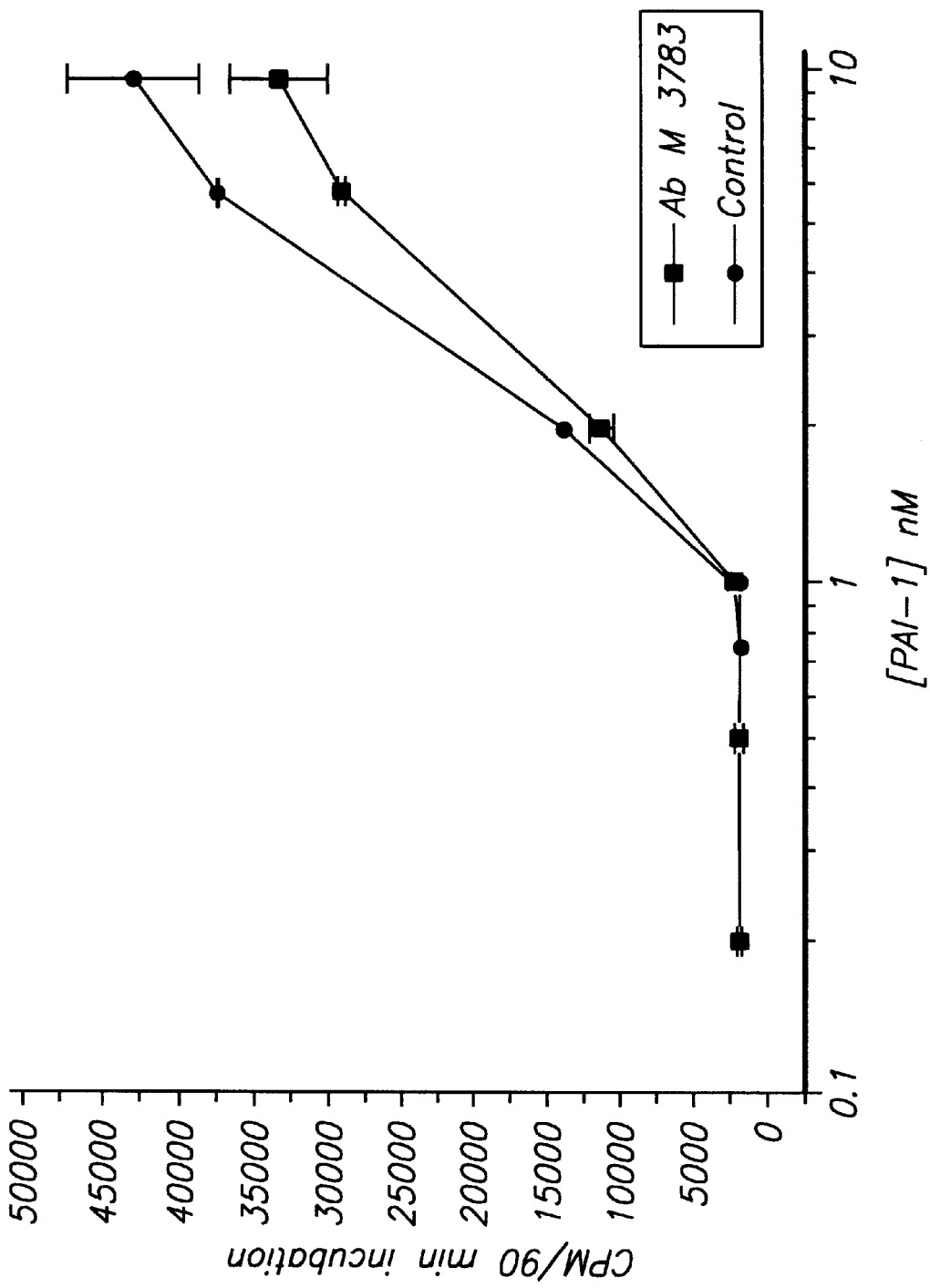
FIG. 3 is a graph showing inhibition of PAI-1 by an anti-PAI-1 monoclonal antibody (Ab). The Y axis represents the total [$^{125}$I]-labeled fibrin remaining within the clot. The X axis represents the effect of a single concentration of tPA in the presence of various concentrations of PAI-1 in the presence or absence of the anti-PAI-1 monoclonal antibody (35 µg/ml).

Effect of Anti-PAI-1 Monoclonal Ab 3783 to Inhibit PAI-1 Titration:

To further demonstrate the versatility of the assay of the invention as a screen for different inhibitor classes, the effect of a monoclonal antibody to functionally inhibit PAI-1 was evaluated. The addition of buffer, platelets and radiolabeled whole blood was as described above. In each reaction tube, 12 IU tPA was added. Reaction tubes were treated with a single concentration of PAI-1 (0.2–10.0 nM) in the presence or absence of 35 $\mu$g monoclonal Ab 3783. After gentle mixing, each tube was treated with 1.25 units thrombin. Reactions were incubated for 90 min. and then processed as described above. Results are illustrated in FIG. 3, a graph illustrating inhibition of PAI-1 by the anti-PAI-1monoclonal antibody. In the graph, the Y axis represents the total [$^{125}$I]-labeled fibrin retained within the clot, while the X axis represents the effect of a single concentration of tPA in the presence of different concentrations of PAI-1 in the presence or absence of the anti-PAI-1 monoclonal antibody (35 $\mu$g/ml). In the presence of anti-PAI-1 Ab, PAI-1 was found to be inhibited by 25%.

Figure 4:
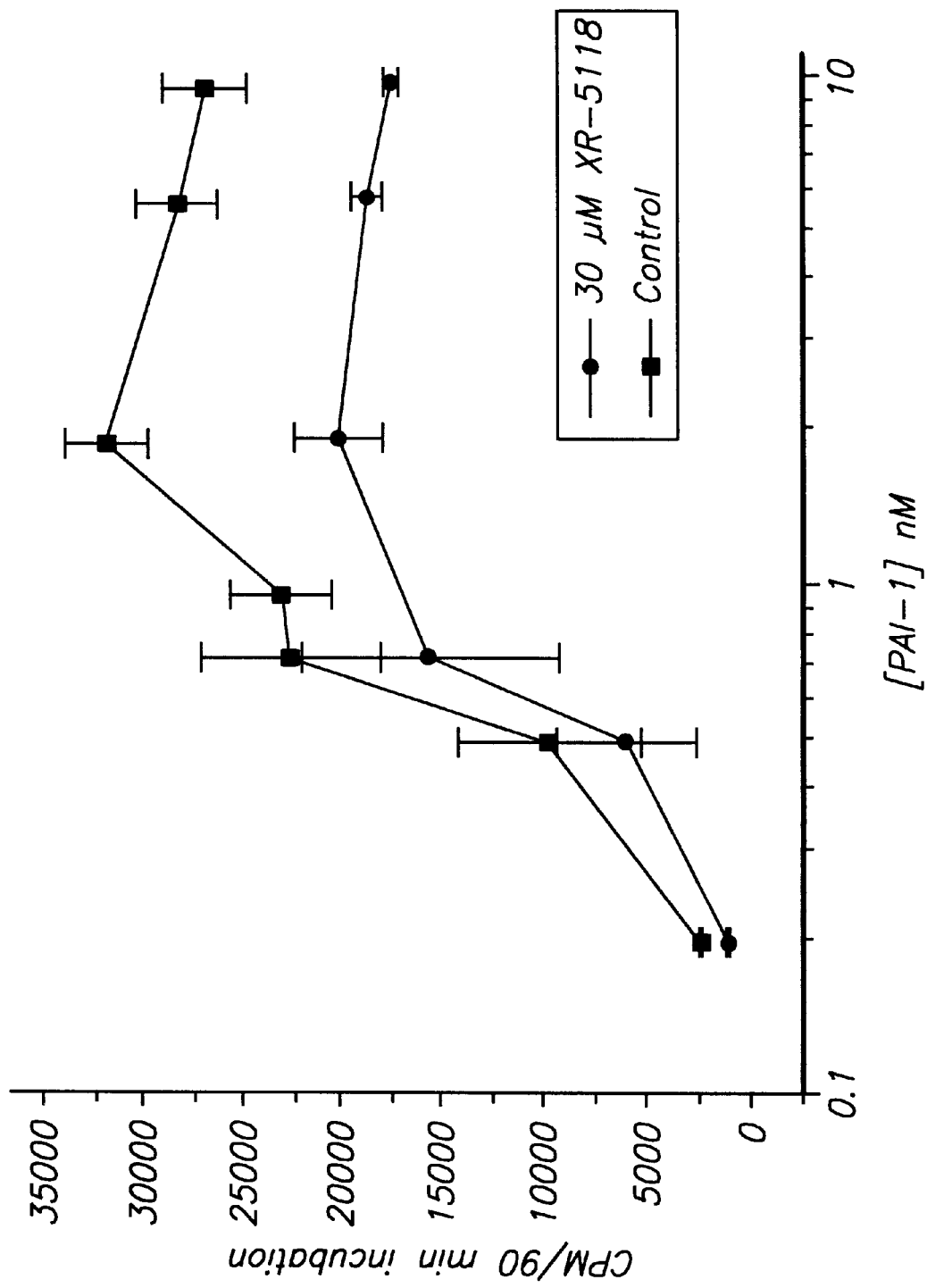
FIG. 4 is a graph showing the effect of the small molecule XR-5118 ((3Z,6Z)-6-benzylidene-3(5-(2-dimethyl aminoethylthio)-2-thienyl) methylene-2,5-piperazinedione, hydrochloride) on PAI-1. The Y axis represents the total [$^{125}$I]-labeled fibrin remaining within the clot after 90 min. The X axis represents the effect of a single concentration of tPA in the presence of increasing concentrations of PAI-1 in the presence or absence of XR-5118 (30 µM).

Effect of Small Molecule PAI-1 Inhibitor XR-5118 on Clot Lysis:

Experiments were carried out to demonstrate the versatility of the assay of the invention to detect the effect of the small molecule XR-5118 on PAI-1. The small molecule XR-5118 is reported to be an inhibitor of PAI-1 and belongs to a class of compounds known as diketopiperazines. See, for example, Charlton et al. (1997), "XR5118, A Novel Modulator of Plasminogen Activator Inhibitor-1 (PAI-1), Increases Endogenous tPA Activity in the Rat," *Fibrinolysis & Proteolysis* 11(1):51–56. XR-5118 ((3Z,6Z)-6-benzylidene-3-(5-(2-dimethylaminoethylthio)-2-thienyl) methylene-2,5-piperazinedione, hydrochloride) was synthesized as described in PCT Publication No. WO 95/32190 (Bryans et al., "Pharmaceutical Diketopiperazine Compounds). The addition of buffer, platelets and radiolabled whole blood was as described above. In each reaction tube 12 IU tPA was added. Reaction tubes were treated with a single concentration of PAI-1 (0.2–10.0 nM) in the presence or absence of 30 $\mu$M XR-5118. After gentle mixing each tube was treated with 1.25 units thrombin. Reaction mixtures were incubated for 90 min. and then processed as described above. Results are illustrated in FIG. 4, a graph illustrating inhibition of PAI-1 by the small molecule XR-5118. In the graph, the Y axis represents the total [$^{125}$I]-labeled fibrin remaining within the clot after 90 min., while the X axis represents the effect of a single concentration of tPA in the presence of increasing concentrations of PAI-1 in the presence or absence of XR-5118 (30 μM). In the presence of XR-5118, PAI-1 activity was found to decrease approximately 35–45%.

Figure 6:
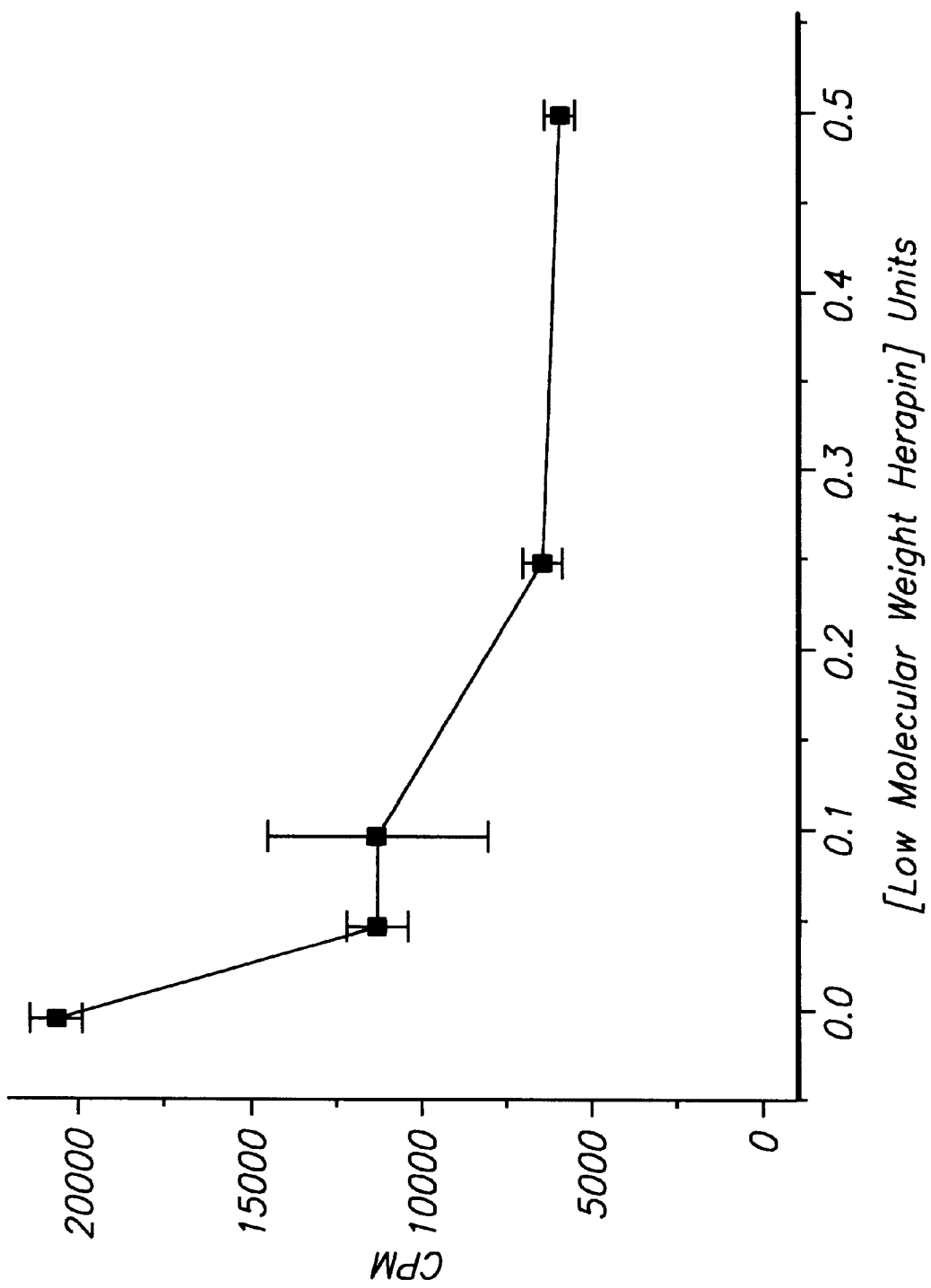
FIG. 6 is a graph showing the effect of low molecular weight heparin on thrombin-induced clot formation. The Y axis represents the total [$^{125}$I]-labeled fibrin remaining within the clot after 90 min. The X axis represents the concentration of heparin used.

Titration of Heparin to Inhibit Thrombin-Stimulated Clot Formation:

This experiment demonstrates the functionality of various bioactive molecules, such as antithrombin, in the assay of the invention, and also demonstrates the use of the assay as a potential screen for inhibitors of thrombin-stimulated clot formation, e.g., heparin. In this assay, the addition of buffer, platelets and [$^{125}$I]-labeled fibrinogen supplemental whole blood was added as described above. A reaction tube was then treated with a single concentration of heparin (0.05–3.0 U/ml), prior to the addition of thrombin (1.25 units). The reaction mixture was incubated for 90 min. and treated as described above. The experiment was carried out three times in duplicate. Results of this experiment showing the effect of low molecular weight heparin on thrombin-induced clot formation are set forth in the graph of FIG. 6. In FIG. 6, the Y axis represents the total [$^{125}$I]-labeled fibrin remaining within the clot after 90 min. The X axis represents the concentration of heparin used.

What is claimed is:

1. A method of screening candidate agents to identify a suitable drug for modulating a component of the mammalian hemostatic system, comprising:
   (a) providing stored whole blood;
   (b) adding unrefrigerated, active platelets to the stored whole blood to provide a screening medium;
   (c) adding a candidate agent to the screening medium; and
   (d) evaluating the ability of the candidate agent to modulate a component of the hemostatic system.

2. The method of claim 1, further comprising the step of diluting the stored whole blood of step (a) prior to step (b).

3. The method of claim 2, wherein the blood is diluted with a physiological buffer.

4. The method of claim 3, wherein physiological buffer comprises a phosphate buffer.

5. The method of claim 3, wherein the blood is diluted at a ratio of blood to buffer in the range of about 1:5 to about 1:20, by volume.

6. The method of claim 5, wherein the blood is diluted at a ratio of about 1:10.

7. The method of claim 1, wherein the ratio of stored whole blood in step (a) to platelets in step (b) is about 1:1 by volume.

8. The method of claim 1, wherein the stored whole blood of step (a) has been stored for about 3 to 21 days.

9. The method of claim 8, wherein the stored whole blood of step (a) has been stored for about 3 to 14 days.

10. The method of claim 1, wherein the stored whole blood of step (a) has been stored at approximately 4° C. to approximately 6° C.

11. The method of claim 10, wherein the stored whole blood of step (a) has been stored at approximately 4° C.

12. The method of claim 1, wherein the ability of the candidate agent to modulate a component of the hemostatic system is evaluated by a decrease in clot formation.

13. The method of claim 1, wherein the ability of the candidate agent to modulate a component of the hemostatic system is evaluated by an increase in clot formation.

14. The method of claim 1, wherein the ability of the candidate agent to modulate a component of the hemostatic system is evaluated by an increase in clot lysis.

15. The method of claim 1, wherein the ability of the candidate agent to modulate a component of the hemostatic system is evaluated by a decrease in clot lysis.

16. The method of claim 15, wherein the candidate agent is an organic compound having a molecular weight in the range of approximately 50 to 2500 Daltons.

17. The method of claim 16, wherein the candidate agent is selected from the group consisting of peptides, saccharides, fatty acids, steroids, purines, and pyrimidines, and structural analogs and combinations thereof.

18. The method of claim 17, wherein the candidate agent is a peptide.

19. The method of claim 18, wherein the peptide is a protease.

20. The method of claim 19, wherein the protease is an activator of clot lysis.

21. The method of claim 1, wherein the candidate agent is a potential inhibitor of plasminogen activator inhibitor (PAI-1).

22. The method of claim 1 further comprising, prior to step (c), adding to the screening medium a compound selected from the group consisting of thrombin, tissue plasminogen activator, fibrinogen, tissue factor, Factors XIIa, XIa, IXa, VIII and Xa.

23. The method of claim 1, further comprising the step of adding labeled fibrinogen to the screening medium prior to step (c).

24. The method of claim 23, wherein the fibrinogen is radioactively labeled.

25. The method of claim 24, wherein the fibrinogen is radioactively labeled with a label selected from the group consisting of $^{125}$I, $^{35}$S, $^{14}$C, $^{32}$P, $^{33}$P and $^{3}$H.

26. The method of claim 23, wherein the fibrinogen is labeled with a fluorescent label.

27. The method of claim 26, wherein the fluorescent label is selected from the group consisting of fluorescein, carboxyfluorescein, fluorescein acrylamide, fluorescein isothiocyanate, coumarin, seminaphthorhodafluorescein, seminaphthofluorescein, naphthofluorescein, hydroxypyrene trisulfonic acid and dichlorofluorescein.

28. The method of claim 27, wherein the fluorescent label is fluorescein.

29. The method of claim 1, wherein the unrefrigerated platelets have been stored for less than 10 days.

30. The method of claim 29, wherein the unrefrigerated platelets have been stored for about 3 to 8 days.

31. The method of claim 1, wherein the amount of whole blood provided in step (a) is about 1 ml and the number of platelets added in step (b) is about $10^6$ to $10^8$.

* * * * *